(12) United States Patent
He et al.

(10) Patent No.: US 6,444,830 B1
(45) Date of Patent: *Sep. 3, 2002

(54) ELECTRON ACCEPTORS FOR POLYMERIC THIN FILM WAVEGUIDE MEDIA

(75) Inventors: Mingqian He, Painted Post, NY (US); Thomas M. Leslie, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/675,967

(22) Filed: Sep. 29, 2000

Related U.S. Application Data

(63) Continuation-in-part of application No. 09/596,069, filed on Jun. 16, 2000.

(51) Int. Cl.$^7$ ............................................. C07D 307/30
(52) U.S. Cl. ........................ 549/474; 558/303; 558/336
(58) Field of Search ..................... 549/474; 558/303, 558/336

(56) References Cited

U.S. PATENT DOCUMENTS

| | | | |
|---|---|---|---|
| 4,767,169 A | 8/1988 | Teng et al. | 350/96.14 |
| 4,795,664 A | 1/1989 | DeMartino | 428/1 |
| 4,810,338 A | 3/1989 | DeMartino et al. | 204/157.88 |
| 4,936,645 A | 6/1990 | Yoon et al. | 350/96.14 |
| 5,006,285 A | 4/1991 | Thackara et al. | 264/1.3 |
| 5,044,725 A | 9/1991 | DeMartino et al. | 385/130 |
| 5,106,211 A | 4/1992 | Chiang et al. | 385/132 |
| 5,133,037 A | 7/1992 | Yoon et al. | 385/132 |
| 5,170,461 A | 12/1992 | Yoon et al. | 385/130 |
| 5,187,234 A | 2/1993 | Leslie et al. | 525/276 |
| 5,196,509 A | 3/1993 | Allen | 528/331 |
| 5,247,042 A | 9/1993 | Allen et al. | 526/310 |
| 5,326,661 A | 7/1994 | Sansone et al. | 430/20 |
| 6,067,186 A | 5/2000 | Dalton et al. | 359/321 |

FOREIGN PATENT DOCUMENTS

| | | |
|---|---|---|
| WO | 98/56749 | 9/1997 |

OTHER PUBLICATIONS

Advanced Organic Chemistry, 3$^{rd}$ Ed., Jerry March, 1985, Table 1, pp. 220–222.

Melikian, G. et al.; Synthesis of Substituted Dicyanomethylendihydrofurans, Synthetic Communications, 25(19), pp. 3045–3051 (1995).

Wang et al., "Design, Synthesis and Characterization of a Novel Substituted Dicyanomethylendihydrofuran Based High–B NLO Chromophore and Its Polymers with Exceptionally High Electro–Optic Coefficients," *Polymer Preprints*, 39(2):1065–1066 (1998).

Zhang et al., "A Novel Trilinkable High $\mu$B NLO Chromophore for Polymeric Electro–optic Material With Enhanced Thermal Stability," *Polymer Preprints*, 40:156–157 (1999).

Ren et al., "A Trifunctionalized High $\mu$B Chromophore and Its 3D Polyurethane Network With Enhanced NLO Alignment Stability for Electro–optic Device Applications," *Polymer Preprints*, 40:160–161 (1999).

Ren, "Electro Active Polymer Thin Films for Fabrication of Ultra–high Bandwidth Integrated Electro–optic Modulators," Ph.D. Thesis, University of Southern California (1999).

Todorova et al., "New NLO Cromophores Based on 2–amino–1,1,3–tricyano–1–propene Acceptor," *Polymeric Materials:Science and Engineering*, 83:256–257 (2000).

*Primary Examiner*—T. A. Solola
(74) *Attorney, Agent, or Firm*—Peter Rogalskyj, Esq.; Walter M. Douglas

(57) ABSTRACT

The present invention is directed to dicyanomethylenedihydrofuran-based electron acceptors which can be used in the preparation of polymeric thin films for waveguide media, and methods of making the same.

22 Claims, No Drawings

ELECTRON ACCEPTORS FOR POLYMERIC THIN FILM WAVEGUIDE MEDIA

This application is a continuation-in-part of co-pending U.S. patent application Ser. No. 09/596,069, filed Jun. 16, 2000.

FIELD OF THE INVENTION

The present invention relates generally to electron acceptors (or withdrawing groups) which can be used in the preparation of polymeric thin films for waveguide media, and specifically to dicyanomethylendihydrofuran-based electron acceptors, and methods of making the same.

BACKGROUND OF THE INVENTION

Thin films of organic or polymeric materials with large second order nonlinearities in combination with silicon-based electronic circuitry can be used in systems for laser modulation and deflection, information control in optical circuitry, as well as in numerous other waveguide applications. In addition, novel processes through third order nonlinearity such as degenerate four-wave nixing, whereby real-time processing of optical fields occurs, have utility in such diverse fields as optical communications and integrated circuit fabrication. The utility of organic materials with large second order and third order nonlinearities for very high frequency application contrasts with the bandwidth limitations of conventional inorganic electrooptic materials currently in use.

Numerous optically responsive monomers and polymers have been developed for use in organic materials which, in turn, can be used in the waveguide applications described above. For example, U.S. Pat. No. 5,044,725, which is incorporated herein by reference in its entirety, describes numerous polymer compositions which provide suitable nonlinear optical response. U.S. Pat. No. 5,044,725 describes, for example, a preferred polymer composition comprising an organic structure containing an electron donating group and an electron withdrawing group at opposing termini of a bridge. To achieve nonlinear optic (NLO) stability, however, thermally stable electron acceptors must be obtained.

Most recently, U.S. Pat. No. 6,067,186 (the '186 patent), disclosed a class of organic chromophores which can result in hardened electro-optic polymers suitable for electro-optic modulators and other devices such as optical switch.

The synthesis of thermally stable electron accepting (or withdrawing) groups for organic nonlinear optical applications are generally known in the art. Although many different electron acceptors have been reported in the literature, few, if any, have showed both suitable thermal stability and very high electron acceptance at the same time. Accordingly, electron acceptors which exhibit both thermal stability and very high electron acceptance are desired.

SUMMARY OF THE INVENTION

The present invention is directed to compounds which can serve as electron acceptors in, for example, thin films for waveguides. Preferred compounds of the invention have Formula (I):

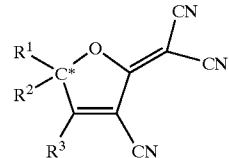

(I)

where $R^1$ and $R^2$ are base stable moieties. $R^1$ can be substituted and unsubstituted $C_1$–$C_{10}$ alkyl, $R^2$ can be substituted and unsubstituted $C_2$–$C_{10}$ alkyl, and $R^1$ and $R^2$ each, independently, can be substituted and unsubstituted $C_4$–$C_{10}$ alkenyl, substituted and unsubstituted $C_4$–$C_{10}$ alkynyl, substituted and unsubstituted aryl, substituted and unsubstituted alkylaryl, substituted and unsubstituted carbocycles, substituted and unsubstituted heterocycles, substituted and unsubstituted cyclohexyl, or $(CH_2)_n$—O—$(CH_2)_n$ where n is 1–10; provided there is no methylene between the * carbon and an sp2 or sp hybridized carbon. Alternatively, $R^1$ and $R^2$ together form a ring structure or a substituted ring structure. $R^3$ is either substituted and unsubstituted $C_1$–$C_5$ alkyl, substituted and unsubstituted $C_1$–$C_5$ alkenyl, substituted and unsubstituted $C_1$–$C_5$ alkynyl. As contemplated herein, the term "alkylaryl" does not include benzyl.

The present invention is also directed to a method of preparing compounds having Formula I comprising the steps 1) providing an alkylvinylether, 2) contacting the alkylvinylether with a strong base to form a first intermediate compound, 3) contacting the first intermediate compound with a ketone to form a second intermediate compound, and 4) reacting the second intermediate compound with dicyanomethane in the presence of a metal alkoxide base, or other appropriate base known to those skilled in the art, to form a compound having Formula I.

As used herein, the phrase "electron acceptor" is used synonymously with "electron accepting group" and "electron withdrawing group", and refers to electronegative organic compounds or substituents which attract electron density from the pi-electron system when the conjugated electron structure is polarized by the input of electromagnetic energy.

DESCRIPTION OF PREFERRED EMBODIMENTS OF THE INVENTION

The present invention relates, in part, to novel electron acceptors which have utility in organic nonlinear optical applications and methods of preparing the same. The compounds of the invention function as electron acceptors (or as electron withdrawing groups) which exhibit both thermal stability and very high electron acceptance simultaneously. The compounds of the invention can be used in, for example, polymeric organic materials for optical waveguides. Such polymeric organic materials are described in, for example, U.S. Pat. Nos. 5,044,725, 4,795,664, 5,247,042, 5,196,509, 4,810,338, 4,936,645, 4,767,169, 5,326,661, 5,187,234, 5,170,461, 5,133,037, 5,106,211, and 5,006,285, each of which is incorporated herein by reference in its entirety.

In preferred embodiments of the invention, the electron acceptor compounds are dicyanomethylenedihydrofuran-based compounds comprising Formula I:

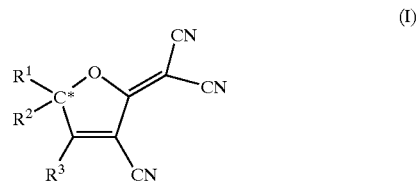

(I)

where, $R^1$ can be substituted and unsubstituted $C_1$–$C_{10}$ alkyl, $R^2$ can be substituted and unsubstituted $C_2$–$C_{10}$ alkyl, and $R^1$ and $R^2$ each, independently, can be selected from the group consisting of substituted and unsubstituted $C_2$–$C_{10}$ alkyl, substituted and unsubstituted $C_4$–$C_{10}$ alkenyl, substituted and unsubstituted $C_4$–$C_{10}$ alkynyl, substituted and unsubstituted aryl, substituted and unsubstituted alkylaryl, substituted and unsubstituted carbocycles, substituted and unsubstituted heterocycles, substituted and unsubstituted cyclohexyl, and $(CH_2)_n$—O—$(CH_2)_n$ where n is 1–10; provided there is no methylene between the * carbon and an sp2 or sp hybridized carbon.

The substituted alkyl, alkenyl, alkynyl, carbocyclic, and heterocyclic groups can comprise one or a plurality of substituents including, for example, fluorine, chlorine, D, and the like. In addition, the heterocyclic groups can comprise O, N, S, and the like.

The aryl groups preferably include, but are not limited to, phenyl, fluorenyl, and naphthyl. The aryl groups, carbocycles, heterocycles, and cyclohexyl can also be substituted by one or a plurality of substituents including, for example, D, halides, including fluorine, chlorine and bromine. The alkylaryl groups preferably comprise $C_1$–$C_{10}$ alkyl and the substituted alkylaryl groups comprise the substitutions for the alkyl and aryl groups described above.

In more preferred embodiments of the invention, $R^1$ and $R^2$ each, independently, are selected from the group consisting of, carbocycle, heterocycle, cyclohexyl, phenyl, cycloalkyl, cycloalkenyl, and substituted phenyl. Additional moieties for $R^1$ and/or $R^2$, independently, include, but are not limited to the following:

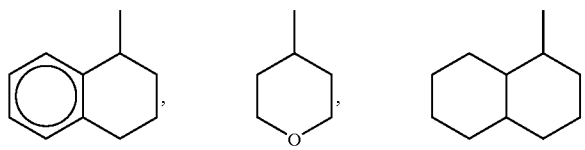

and the like.

In even more preferred embodiments of the invention, $R^1$ is $CH_3$ and $R^2$ is a substituted phenyl. Preferably, the substituted phenyl is selected from the group consisting of, but not limited to:

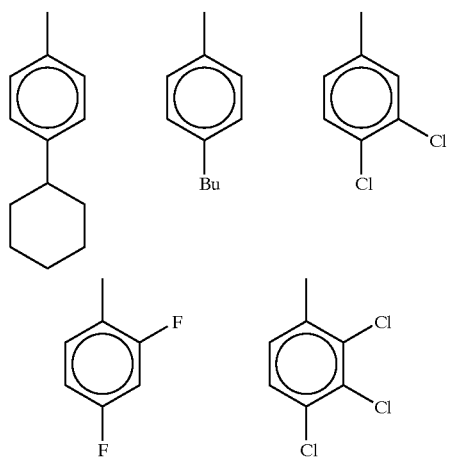

and the like.

Alternatively, $R^1$ and $R^2$ together form a ring structure or a substituted ring structure from 3 to 7 atoms total with 5 or 6 atoms being preferred. Preferably, the ring structure is substituted or unsubstituted carbocycle, substituted or unsubstituted heterocycle, or substituted or unsubstituted cyclohexyl. The substituted ring structure can comprise substituents including, but not limited to, halides, including fluorine, chlorine and bromine. A preferred compound having a ring structure formed by $R^1$ and $R^2$ comprises

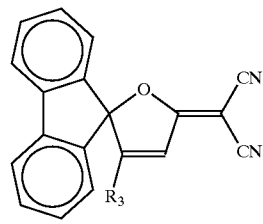

$R^3$ is preferably selected from the group consisting of substituted and unsubstituted $C_1$–$C_4$ alkyl, substituted and unsubstituted $C_1$–$C_4$ alkenyl, substituted and unsubstituted $C_1$–$C_4$ alkynyl. More preferably, $R_3$ is $C_3$ alkenyl (-CH=CH-$CH_3$), $C_5$ alkenyl (—CH=CH—CH=CH—$CH_3$), $C_2$ alkynyl (—C≡CH), or $C_4$ alkynyl (—≡C—C≡CH). Most preferably, $R^3$ is $CH_3$. The substituted alkyl, alkenyl, and alkynyl groups can comprise one or a plurality of substituents including, for example, F, D, or Cl.

In preferred embodiments of the invention, $R_3$ is selected from the group consisting of $C_1$–$C_4$ alkyl, $C_1$–$C_4$ alkenyl, and $C_1$–$C_4$ alkynyl. In more preferred embodiments of the invention, $R^3$ is $CH_3$.

The present invention is also directed to methods of preparing electron acceptors of the invention. In a particularly preferred embodiment of the compound of Formula I, $R^3$ is $CH_3$, and the product can be prepared by the following steps depicted in Scheme I: a) providing an alkylvinylether, b) contacting the alkylvinylether with a strong base to form a first intermediate compound, c) contacting the first intermediate compound with a ketone to form a second intermediate compound, and d) reacting the second intermediate compound with dicyanomethane in the presence of a second base to form a compound having Formula I.

Scheme I

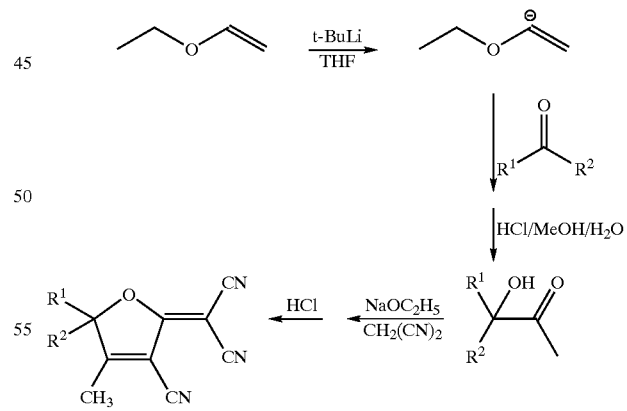

Compounds having an $R^3$ moiety other than $CH_3$ can be prepared by substituting the appropriate starting compound as is well known to persons skilled in the art. Each of the above mentioned steps is described in greater detail below.

In preferred embodiments of the invention, an alkylvinylether in a solvent is the starting material. The solvent is, preferably, tetrahydrofuran (THF), 1,4-dioxane, or the like. Although the alkylvinylether depicted in Scheme I is ethylvinylether, other alkylvinylethers can be used. The alkylvinylether preferably comprises the formula CH$_3$—(CH$_2$)$_x$—O—CH=CHR$^4$, where x is 1–3 and R$^4$ is H or C$_1$-C$_4$ alkyl. Most preferably, the alkylvinylether is methylvinylether or ethylvinylether.

The alkylvinylether is contacted with a strong base to form a first intermediate compound. Preferably, the strong base has a pK$_a$ greater than the ethylinic C-H bond α to the oxygen function of the alkylvinylether. For example, see Advanced Organic Chemistry, Third Ed., Jerry March, 1985, Table 1, pp. 220–222. In preferred embodiments of the invention, the strong base is an alkyl lithium, or an alkali metal salt of an alkyl anion, including, but not limited to, t-BuLi or sec-BuLi. The alkylvinylether is preferably contacted with the strong base between about −70° C. and −85° C., most preferably at about −78° C.

The first intermediate compound is contacted with a ketone and then an acid/alcohol/water solution to form a second intermediate compound. Numerous acid/alcohol/water solutions known to those skilled in the art can be used in the present invention. The acid/alcohol/water solution is preferably HCl/MeOH/H$_2$O, HBr/EtOH/H$_2$O, or H$_2$SO$_4$/EtOH/H$_2$O. Preferably, the contacting is at room temperature. Preferably, the pH is adjusted between 1 and 4.

Preferably, the ketone comprises the formula

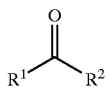

wherein R$^1$ can be substituted and unsubstituted C$_1$-C$_{10}$ alkyl, R$_2$ can be substituted and unsubstituted C$_2$-C$_{10}$ alkyl, and R$^1$ and R$^2$ each, independently, can be selected from the group consisting of, substituted and unsubstituted C$_1$-C$_{10}$ alkyl, substituted and unsubstituted C$_1$-C$_{10}$ alkenyl, substituted and unsubstituted C$_1$-C$_{10}$ alkynyl, substituted and unsubstituted aryl, substituted and unsubstituted alkylaryl, substituted and unsubstituted carbocycles, substituted and unsubstituted heterocycles, substituted and unsubstituted cyclohexyl, and (CH$_2$)$_n$—O—(CH$_2$)$_n$ where n is 1–10. Alternatively, R$^1$ and R$^2$ together form a ring structure or a substituted ring structure, as described above.

Preferably, the C=C and C≡C bonds of the alkenyl and alkynyl groups are not immediately adjacent the carbonyl group of the ketone compound.

The substituted alkyl, alkenyl, and alkynyl groups can comprise one or a plurality of substituents including, for example, fluorine, D, and chlorine.

The aryl groups preferably include, but are not limited to, fluorenyl, phenyl, and naphthyl. The aryl groups, carbocycle groups, heterocycle groups, and cyclohexyl can also be substituted by, for example, D, halides, including fluorine and chlorine. Preferably, the alkylaryl groups comprise C$_1$-C$_{10}$ alkyl and the substituted alkylaryl groups can comprise the substituents for the alkyl and aryl groups described above.

In more preferred embodiments of the invention, R$^1$ and R$_2$ each, independently, are selected from the group consisting of, cyclohexyl, phenyl, and substituted phenyl.

In even more preferred embodiments of the invention, R$^1$ is CH$_3$ and R$^2$ is a substituted phenyl. Preferably, the substituted phenyl is selected from the following:

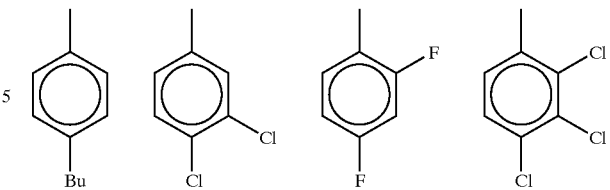

Alternatively, R$^1$ and R$^2$ together form a ring structure or a substituted ring structure or a heterocyclic ring structure. Preferably, the ring structure is substituted or unsubstituted 5 or 6 member rings, including, but not limited to, 5 or 6 member heterocyclic rings and fluorenyl. The substituted ring structure can comprise substituents including, but not limited to, halides, including fluorine, chlorine and D.

The second intermediate compound is reacted with dicyanomethane in the presence of a second base at the appropriate temperature to form a compound having Formula I. The second base is preferably a metal alkoxide including, but not limited to, NaOC$_2$H$_5$, NaOH, KOH, and K$_2$CO$_3$. After contacting the second intermediate compound with dicyanomethane in the presence of a second base, dilute acid such as, for example, HCl, is added for neutralization of the resultant electron acceptor compound.

The invention is further illustrated by way of the following examples which are intended to elucidate the invention. These examples are not intended, nor are they to be construed, as limiting the scope of the disclosure.

EXAMPLES

Example 1

General Synthesis Of Dicyanomethylenedihydrofurans

To a solution of 0.33 mol of ethyl vinyl ether in 150 ml of dry THF, 0.3 mol of t-BuLi in pentane was added dropwise at −78° C. The mixture was stirred and allowed to warm up slowly 0° C. and subsequently cooled to −78° C. again. Next, 0.25 mol of cyclohexyl phenyl ketone dissolved in a minimum of dry THF was added dropwise. The mixture was stirred overnight at room temperature, then acidified using HCl/MeOH/THF/H$_2$O solution to pH 1–4. After stirring this mixture for two hours, most of the solvent mixture was evaporated using a rotary evaporator. The rest of the mixture was extracted with ethyl ether (3×100 ml). The organic solution was washed with NaHCO$_3$, brine, and DI water. This mixture was then dried over anhydrous MgSO$_4$. After evaporating the ether, the cruded product was purified by column chromatography (5% ethyl acetate in hexane) to give pure alpha-hydroxy ketone (30 g).

The hydroxy ketone synthesized above (0.02 mol) was mixed with malononitrile (0.04 mol) in ethyl alcohol cooled in an ice bath. To this, 20 ml of 1 M NaOC$_2$H$_5$/EtOH was added dropwise. The mixture was allowed to stir overnight. After neutralization by concentrated HCl to pH 6, the solvent was evaporated by vacuum. The rest of the solid was dissolved into CH$_2$Cl$_2$ and filtered to remove the undissolved solid. After evaporating the CH$_2$Cl$_2$, the crude product was purified by recrystalization from ethanol to give the dicyanomethylenedihydrofuran compound (1.25 g).

Alternatively, and more preferably, the hydroxy ketone synthesized above (0.02 mol) was mixed with malononitrile (0.04 mol) and potassium carbonate (0.02 mol) in THF (40 ml) and EtOH (2 ml). To this mixture, a catalytic amount of 18-crown ether was added. The mixture was stirred and allowed to reflux overnight. The solid was filtered off, followed by evaporation of most of the solvent. The crude mixture was purified by colum chromatography ($CH_2Cl_2$) to give the dicyanomethylenedihydrofuran compound (1.5 g).

Example 2

Preparation of a Dicyanomethylenedihydrofuran-based Electron Acceptor

To a solution of ethyl vinyl ether (28.8 g in 300 ml of THF) was added 176 ml of t-BuLi dropwise at −78° C. The mixture was slowly warmed to 0° C. and subsequently cooled to −78° C. again. Cyclohexanone (30 g in 30 ml of THF) was added dropwise and the mixture was slowly warmed to room temperature and stirred for an additional four hours. A solution of methanol (70 ml), water (20 ml) and conc. HCl(10 ml) was slowly added until a pH of about 2–3 was obtained. The mixture was stirred overnight at room temperature and neutralized to pH 7 by addition of $NaHCO_3$ and water and the solvent was evaporated. The residual solvent was extracted by ether (100 ml). The solid was washed with $NaHCO_3$ (50 ml), brine (100 ml), and dried over $MgSO_4$. Vacuum distillation of the intermediate yielded 36 g. The residue was dissolved in EtOH, $CH_2Cl_2$ extracted, and salt precipitated. The rest of the mixture was recrystallized from ethanol (150 ml) to give 6.1 g of the final compound.

Example 3

Preparation of a Dicyanomethylenedihydrofuran-based Electron Acceptor

To a solution of ethylvinylether (21.6 g in 300 ml of THF) was added 110 ml of t-BuLi dropwise at −78° C. The mixture was warmed to 0° C. and subsequently cooled to −78° C. again. 5', 4'-dichloroacetophenone (30.5 g) was dissolved into 150 ml of THF and then added dropwise. This mixture was run overnight at room temperature. A solution of HCl (10 ml), methanol (70 ml), and water (20 ml) was added after the reaction was finished. The mixture was adjusted to pH 4 and allowed to stir overnight. $NaHCO_3$ was added to neutralize this solution to about pH 7. The water phase was separated and the organic phase was evaporated to yield a solid. The residual solvent was extracted by ether (100 ml). The solid was washed with saturated $NaHCO_3$ (50 ml), brine (100 ml), and dried over $MgSO_4$. Vacuum distillation of the intermediate yielded 55 g. The residue was dissolved in EtOH, $CH_2Cl_2$ extracted, and salt precipitated. The rest of the mixture was recrystallized from ethanol (150 ml) to give 5.5 g of the final compound.

Although the invention has been described in detail for the purpose of illustration, it is understood that such detail is solely for that purpose, and variations can be made therein by those skilled in the art without departing from the spirit and scope of the invention which is defined by the following claims.

What is claimed is:
1. A compound having Formula I:

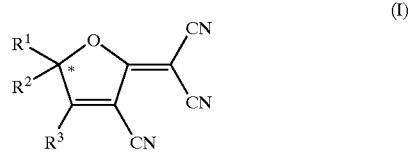

wherein:
$R^1$ is a $C_1$–$C_{10}$ alkyl substituted with one or more substituents selected from the group consisting of fluorine and chlorine and wherein $R^2$ is selected from the group consisting of substituted and unsubstituted $C_1$–$C_{10}$ alkyl, substituted and unsubstituted $C_2$–$C_{10}$ alkenyl, substituted and unsubstituted $C_2$–$C_{10}$ alkynyl, and $(CH_2)_n$—O—$(CH_2)_n$ where n is 1–10; and $R^3$ is selected from the group consisting of substituted and unsubstituted $C_1$–$C_4$ alkyl, substituted and unsubstituted $C_1$–$C_4$ alkenyl, and substituted and unsubstituted $C_1$–$C_4$ alkynyl.

2. The compound of claim 1, wherein $R^1$ is a $C_1$–$C_{10}$ alkyl substituted with a plurality of fluorines and wherein $R^2$ is an unsubstituted $C_1$–$C_{10}$ alkyl.

3. The compound of claim 1, wherein $R_1$ represents a $C_1$–$C_{10}$ alkyl substituted with one or more substituents selected from the group consisting of fluorine and chlorine and wherein $R^2$ represents a different $C_1$–$C_{10}$ alkyl substituted with one or more substituents selected from the group consisting of fluorine and chlorine.

4. The compound of claim 1, wherein $R_1$ represents a $C_1$–$C_{10}$ alkyl substituted with a plurality of fluorines and wherein $R^2$ represents a different $C_1$–$C_{10}$ alkyl substituted with a plurality of fluorines.

5. The compound of claim 1, wherein $R^2$ is an unsubstituted $C_1$–$C_{10}$ alkyl.

6. The compound of claim 1, wherein $R^2$ is an substituted $C_1$–$C_{10}$ alkyl.

7. The compound of claim 1, wherein $R^2$ is a substituted or unsubstituted $C_2$–$C_{10}$ alkenyl containing a sp2 hybridized carbon or a substituted or unsubstituted $C_2$–$C_{10}$ alkynyl containing a sp hybridized carbon; and wherein the sp2 or sp hybridized carbon is bonded directly to the * carbon via a single bond.

8. The compound of claim 1, wherein the substituted or unsubstituted $C_2$–$C_{10}$ alkenyl is a substituted or unsubstituted $C_4$–$C_{10}$ alkenyl and wherein the substituted or unsubstituted $C_2$–$C_{10}$ alkynyl is a substituted or unsubstituted $C_4$–$C_{10}$ alkynyl.

9. The compound of claim 1, wherein $R^2$ is a substituted or unsubstituted $C_4$–$C_{10}$ alkenyl containing a sp2 hybridized carbon or a substituted or unsubstituted $C_4$–$C_{10}$ alkynyl containing a sp hybridized carbon; and wherein the sp2 or sp hybridized carbon is bonded directly to the * carbon via a single bond.

10. The compound of claim 1, wherein, when $R^1$ and/or $R^2$ contains a sp2 or sp hybridized carbon, the sp2 or sp hybridized carbon is bonded directly to the * carbon via a single bond.

11. A method of preparing a compound according to claim 1, said method comprising:

a) providing an alpha-hydroxy ketone having the formula:

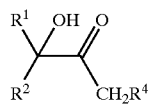

wherein $R^1$ and $R^2$ are defined as in claim 1 and wherein $R^4$ is H or $C_1$–$C_4$ alkyl; and b) reacting said alpha-hydroxy ketone with a dicyanomethane in the presence of a base to form a compound according to claim 1.

12. The method of claim 11, wherein the alpha-hydroxy ketone has the formula:

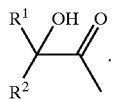

13. The method of claim 11, wherein $R^1$ is a $C_1$–$C_{10}$ alkyl substituted with a plurality of fluorines and wherein $R^2$ is an unsubstituted $C_1$–$C_{10}$ alkyl.

14. The method of claim 11, wherein $R^1$ represents a $C_1$–$C_{10}$ alkyl substituted with one or more substituents selected from the group consisting of fluorine and chlorine and wherein $R^2$ represents a different $C_1$–$C_{10}$ alkyl substituted with one or more substituents selected from the group consisting of fluorine and chlorine.

15. The method of claim 11, wherein $R^1$ represents a $C_1$–$C_{10}$ alkyl substituted with a plurality of fluorines and wherein $R^2$ represents a different $C_1$–$C_{10}$ alkyl substituted with a plurality of fluorines.

16. The method of claim 11, wherein $R^2$ is an unsubstituted $C_1$–$C_{10}$ alkyl.

17. The method of claim 11, wherein $R^2$ is an unsubstituted $C_1$–$C_{10}$ alkyl.

18. The method of claim 11, wherein $R^2$ is a substituted or unsubstituted $C_2$–$C_{10}$ alkenyl containing a sp2 hybridized carbon or a substituted or unsubstituted $C_2$–$C_{10}$ alkynyl containing a sp hybridized carbon; and wherein the sp2 or sp hybridized carbon is bonded directly to the * carbon via a single bond.

19. The method of claim 11, wherein the substituted or unsubstituted $C_2$–$C_{10}$ alkenyl is a substituted or unsubstituted $C_4$–$C_{10}$ alkenyl and wherein the substituted or unsubstituted $C_2$–$C_{10}$ alkynyl is a substituted or unsubstituted $C_4$–$C_{10}$ alkynyl.

20. The method of claim 11, wherein $R^2$ is a substituted or unsubstituted $C_4$–$C_{10}$ alkenyl containing a sp2 hybridized carbon or a substituted or unsubstituted $C_4$–$C_{10}$ alkynyl containing a sp hybridized carbon; and wherein the sp2 or sp hybridized carbon is bonded directly to the * carbon via a single bond.

21. The method of claim 11, wherein, when $R^1$ and/or $R^2$ contains a sp2 or sp hybridized carbon, the sp2 or sp hybridized carbon is bonded directly to the * carbon via a single bond.

22. The method of claim 11, wherein said second base is a metal alkoxide.

* * * * *